United States Patent [19]

Drucker

[11] 4,389,394
[45] Jun. 21, 1983

[54] METHODS FOR REDUCING DENTAL CARIES

[75] Inventor: David B. Drucker, Alderley Edge, England

[73] Assignee: Talres Development (N.A.) N.V., Netherlands Antilles

[21] Appl. No.: 343,286

[22] Filed: Jan. 27, 1982

Related U.S. Application Data

[63] Continuation of Ser. No. 139,474, Apr. 11, 1980, abandoned, which is a continuation-in-part of Ser. No. 954,929, Oct. 26, 1978, abandoned.

[30] Foreign Application Priority Data

Sep. 22, 1978 [GB] United Kingdom ............... 37840/78

[51] Int. Cl.$^3$ ..................... A61K 7/20; A61K 31/70
[52] U.S. Cl. ........................................ 424/53; 424/49; 424/180
[58] Field of Search ............... 424/180, 49, 53; 530/122

[56] References Cited

U.S. PATENT DOCUMENTS

| | | | |
|---|---|---|---|
| 3,932,604 | 1/1976 | Barth | 424/49 |
| 3,962,417 | 6/1976 | Howell | 424/49 |
| 4,117,224 | 9/1978 | Khan et al. | 536/122 |

FOREIGN PATENT DOCUMENTS 2700036 3/1977 Fed. Rep. of Germany .
2700917 7/1977 Fed. Rep. of Germany .

Primary Examiner—Blondel Hazel
Attorney, Agent, or Firm—Ostrolenk, Faber, Gerb & Soffen

[57] ABSTRACT

A use in human therapy (viz as an active ingredient for inhibiting tooth decay, for reducing acidogenesis by mouth flora, and for reducing adhesion to dental surfaces of mouth flora and reducing plaque formation on dental surfaces) has been found for chlorodeoxysucrose derivatives of the general formula

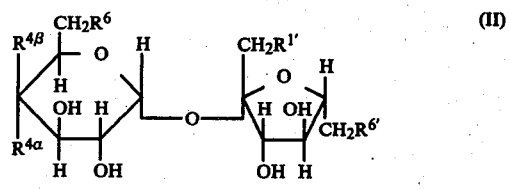

(II)

(wherein: $R^{4\alpha}$ is a hydroxy group and $R^{4\beta}$ is a hydrogen atom, or, one of $R^{4\alpha}$ and $R^{4\beta}$ is a hydrogen atom and the other is a chlorine atom; $R^6$ is a hydroxy group or, if at least one of $R^{4\alpha}$, $R^{4\beta}$ or $R^1$ is a chlorine atom, then it is a hydroxy group or a chlorine atom; $R^{1'}$ is a hydroxy group or a chlorine atom; and $R^{6'}$ is a hydroxy group, or if at least one of $R^{4\alpha}$, $R^{4\beta}$ or $R^1$ is a chlorine atom, then it is a hydroxy group or a chlorine atom).

8 Claims, No Drawings

METHODS FOR REDUCING DENTAL CARIES

This is a continuation of application Ser. No. 139,474, filed Apr. 11, 1980 now abandoned, which in turn is a continuation-in-part of application Ser. No. 954,929, filed Oct. 26, 1978, now abandoned.

SUMMARY OF THE INVENTION

This invention relates to substances of use in preventing tooth decay.

The substances employed by the invention are chlorodeoxysucrose derivatives. The derivatives of the invention have the effect of lessening the acid formation by the mouth flora, for example *Streptococcus mutans*, and of reducing the tendency of the cells to adhere to the tooth surface.

Accordingly, it is an object of the invention to provide a method of reducing the degree of dental caries caused by carbohydrate food products by contacting the mouth with a chlorodeoxy sucrose derivative during, previous to or soon after a carbohydrate food product is ingested.

BACKGROUND OF THE INVENTION

In tooth decay, also known as dental caries, the enamel and thereafter the dentine are etched away until the internal pulp is reached. Eventually the tooth may die. Caries appear to be caused by acid released when bacteria in the mouth utilise carbohydrates such as sucrose. Examples of the bacteria involved include Streptococcus spp.

It is possible to reduce the incidence of caries by regular exposure of the teeth to fluoride ions. Such ions react with the enamel and render it more resistant to etching by acid. However, there is a strong feeling in the UK and elsewhere that it is not right to enforce mass medication on the population by addition of fluoride to water supplies.

It is accepted that regular cleaning of the teeth can lead to a more healthy dentition. A further way of lessening the chance of tooth decay is to reduce the carbohydrate intake, especially the amount of sucrose in the diet. For this reason there is a growing market for artificial sweeteners which can replace the sucrose and are non-cariogenic (i.e. do not cause caries).

It is important at this stage to distinguish between non-cariogenic and anticariogenic behaviour. A substance is non-cariogenic if it does not contribute to the incidence of caries. Thus, for example, low-calorie sweeteners such as saccharin are non-cariogenic. Low-sugar foodstuffs and related products containing these sweeteners cause less tooth decay because, for the same sweetness, their content of cariogenic material has been largely substituted by the non-cariogen.

A substance is anticariogenic, on the other hand, if it can reduce the cariogenicity of a product by virtue of the addition of the substance to the product. Anticariogenic substances can thus help avoid the need to lower the carbohydrate content of a product in order to lower its cariogenicity.

West German Offenlegungsschrift No. 2700036 is described the use of a group of chlorodeoxysucrose derivatives as artificial sweetening agents. This group comprises sucrose derivatives of the general formula

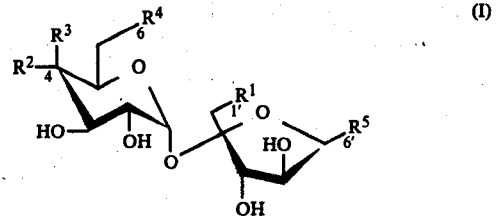

in which
R$^1$ represents a hydroxy group or a chlorine atom;
R$^2$ and R$^3$ respectively represent a hydroxy group and a hydrogen atom, a chlorine atom and a hydrogen atom, or a hydrogen atom and a chlorine atom, the 4-position being the D-configuration;
R$^4$ represents a hydroxy group; or, if at least two of R$^1$, R$^2$, R$^3$ and R$^5$ represent chlorine atoms, R$^4$ represents a hydroxy group or a chlorine atom; and
R$^5$ represents a hydroxy group or a chlorine atom;
provided that at least one of R$^1$, R$^2$, R$^3$ and R$^5$ represents a chlorine atom.

The hope was that these compounds could be used to replace at least part of the sucrose in the diet, and thereby act as non-cariogenic materials.

Particular examples of compounds of the above general formula (I) are as follows (the systematic name is given first, followed by a trivial name using "galactosucrose" in those cases where an inverted 4-chloro substituent is present):

1. 1'-chloro-1'-deoxysucrose
2. 4-chloro-4-deoxy-α-D-galactopyranosyl-β-D-fructofuranoside [ie 4-chloro-4-deoxygalactosucrose]
3. 4-chloro-4-deoxy-α-D-galactopyranosyl-1-chloro-1-deoxy-β-D-fructofuranoside [ie 4,1'-dichloro-4,1-4,1'-dideoxygalactosucrose]
4. 1',6'-dichloro-1',6'-dideoxysucrose
5. 4-chloro-4-deoxy-α-D-galactopyranosyl-1,6-dichloro-1,6-dideoxy-β-D-fructofuranoside [ie 4,1',6'-trichloro-4,1',6'-'-trideoxygalactosucrose]
6. 4,6-dichloro-4,6-dideoxy-α-D-galactopyranosyl-6-chloro-6-deoxy-β-D-fructofuranoside [ie 4,6,6'-trichloro-4,6,6'-trideoxygalactosucrose]
7. 6,1',6'-trichloro-6,1',6'-trideoxysucrose
8. 4,6-dichloro-4,6-dideoxy-α-D-galactopyranosyl-1,6-dichloro-1,6-dideoxy-β-D-fructofuranoside [ie 4,6,1',6'-tetrachloro-4,6,1',6'-tetradeoxygalactosucrose]
9. 4,6,1',6'-tetrachloro-4,6,1',6'-tetradeoxysucrose.

Unexpectedly, I have now found that not only do compounds such as the compounds no. 1 to no. 9 appear to fulfil the hope of non-cariogenicity, but also they exhibit an anticariogenic effect when retained in the mouth.

More specifically, I have found that there is a group of chlorodeoxysucroses which can reduce the amount of acid produced by mouth bacteria and which can reduce the adhesion of bacterial cells to dental surfaces.

DETAILED DESCRIPTION OF THE INVENTION

The finding of anticariogenic activity leads to a method of preventing or limiting dental caries by administering to the subject a regular oral intake of a chlorodeoxysucrose derivative and this forms one feature of this invention.

Another feature of the invention is the reduction of acidogenesis by mouth flora such as *S. mutans* in the presence of a carbohydrate by contacting the flora with a chlorodeoxysucrose derivative.

A further feature of the invention is the reduction of adhesion of cells of mouth flora such as *S. mutans* to dental surfaces and reduction in plaque formation thereon, by contacting the teeth with a chlorodeoxysucrose derivative.

The chlorodeoxysucrose derivatives of the invention have the general formula

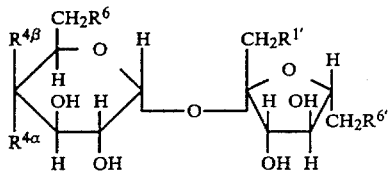

(II)

wherein:

$R^{4\alpha}$ is a hydroxy group and $R^{4\beta}$ is a hydrogen atom, or, one of $R^{4\alpha}$ and $R^{4\beta}$ is a hydrogen atom and the other is a chlorine atom;

$R^6$ is a hydroxy group or, if at least one of $R^{4\alpha}$, $R^{4\beta}$ or $R^{1'}$ is a chlorine atom, then it is a hydroxy group or a chlorine atom;

$R^{1'}$ is a hydroxy group or a chlorine atom; and $R^{6'}$ is a hydroxy group or, if at least one of $R^{4\alpha}$, $R^{4\beta}$ or $R^{1'}$ is a chlorine atom, then it is a hydroxy group or a chlorine atom.

Compounds of the formula (II) possess the ability to interfere with sucrose-mediated adherence of bacterial cells to teeth, as well as the ability to interfere with sucrose-mediated acidogenisis (ie acid-production) by bacteria in the mouth.

Possibly the compounds (II) are substrates for sucrose receptor sites on bacterial extracellular and membrane-bound proteins. Using radiolabelled material, evidence has been found that the compounds (II) inhibit nucleic acid synthesis by mouth bacteria, resulting in the accumulation of low molecular weight products.

The compounds of formula (II) can be mono-, di-, tri- or tetrachloro derivatives of sucrose or (where $R^{4\beta}$ is a chlorine atom) of D-galactose.

For a monochloro derivative, it is preferred that $R^{1'}$ is the chlorine atom. For dichloro derivatives, it is preferred that $R^{1'}$ and $R^{6'}$ are the chlorine atoms. For trichloro derivatives, it is preferred that $R^{6'}$ is one of the chlorine atoms, with the other two chlorine atoms preferably then being provided by any two of (i) $R^{4\alpha}$ or $R^{4\beta}$, (ii) $R^6$ and (iii) $R^{1'}$. Particularly preferred trichloro derivatives are those wherein $R^6$, $R^{1'}$ and $R^{6'}$, or $R^{4\beta}$, $R^{1'}$ and $R^{6'}$ are the chlorine atoms, with the latter combination being the most preferred trichloro derivative and indeed the most preferred compound of general formula (II).

More generally, it is preferred that when one of $R^{4\alpha}$ and $R^{4\beta}$ is a chlorine atom, then it is $R^{4\beta}$ which is the chlorine. Compounds (II) wherein $R^{1'}$ is chlorine show most promise, particularly when there are one or two other chlorines provided by $R^{4\beta}$, $R^6$ or $R^{6'}$.

A chlorodeoxysucrose derivative (II) may, as desired be incorporated in otherwise cariogenic foodstuffs and beverages, where if sweet it may also serve the purpose of sweetening the product. Alternatively, it may be administered separately, e.g. in the form of tablets to be sucked or chewed, or as a mouthwash or as a material to be added to the foodstuff or beverage before ingestion.

Examples of compositions in accordance with the invention include not only the tablets and mouthwashes, but also toothpaste, chewing gum and other products which have been formulated to take advantage of the anti-cariogenic properties of the compounds (II). An appropriate level of compound (II) can be determined having regard to the properties of the particular compound which is selected and the type of product to be prepared.

It is not possible to be precise regarding the level of compound (II) to be employed; much will depend on the properties of the other ingredients with which it is mixed to prepare the composition of the invention.

Use can simultaneously be made of any sweetening characteristics possessed by the compounds (II), but for preference, the level of the compound should be less than $15.(x)^{-1}$ weight percent, where x is the sweetening power of the compound (II). The sweetening power x is assessed by a serial dilution procedure using comparison with 10% sucrose solution to determine the concentration required to produce a solution of the compound (II) isosweet with the 10% sucrose.

As described in West German Offenlegungsschrift No. 2700036, the compounds nos. 3,4,5,7,8 and 9 are many times sweeter than sucrose. For the present purposes, it is preferred to employ such sweet compounds at relatively low levels, e.g. at less than 0.1 wt.% of the dental composition.

On the other hand, the compounds nos. 1, 2 and 6 of the Offenlegungsschrift do not possess such strong sweetening action. Compounds of formula (II) which are less than 10 times sweeter than sucrose (i.e. compounds whose 1% solutions are not as sweet as 10% sucrose solution) can be employed at higher levels in the present dental compositions, and may form up to 1% or more of the composition.

In general, the compounds (II) will be formulated as dental compositions using various conventional formulation aids. Examples of these aids include solid or liquid carriers, flavour and colour additives, and other active ingredients. Depending on the type of product to be made, it may also be appropriate to include humectants, surfactants, thickening agents, binders or other known ingredients.

Chlorodeoxy derivatives of sucrose are known in general. They may be obtained by reacting a suitably protected sucrose with a chlorinating reagent which introduces a chlorine atom at the or each desired position. Such reagents can replace a free hydroxy group by a chlorine atom or can react with an esterified hydroxy group to introduce the chlorine. Positions requiring protection may for example be esterified or blocked with acetal or ether groups which can be easily removed after chlorination. Typical reagents include sulphuryl chloride to form the chlorosulphate ester which ester on treatment with chloride ions in turn gives the chlorodeoxy derivatives. Further details of suitable preparative methods are given for example in our German Offenlegungsschrift No. 2700036 and in the literature mentioned therein.

The available toxicity data indicates that the chlorodeoxysucroses are of very low toxicity. For example, in the rat the compound no. 5 mentioned above has an $LD_{50}$ of more than 16 g/kg, being the maximum dose that it is practically possible to administer per os.

The efficacy of the chlorodeoxysucrose derivatives of formula (II) is shown by the following experimental work. The experiments (A) and (B) describe work on pH reduction and adherence; experiments (C) and (D) extend this work to show the generality of the effect for the derivatives of formula (II); experiment (E) describes in vivo animal tests; and experiments (F) and (G) are part of the trials now being carried out using human volunteers.

(A) Effect on Reduction of pH by *Streptococcus mutans*:

Mouth flora such as *S. mutans* cause dental caries by producing acid which erodes the tooth enamel. The cells exude a polysaccharide which firmly adheres them to the tooth surfaces as plaque, thus enhancing the local erosion by the acid. The effect of chlorodeoxysucroses on acid production by *S. mutans* in sucrose solutions was studied in comparison with the effect produced by xylitol, an agent proposed as a caries preventative.

The experiments were effected by adding washed, standardised suspensions of exponential-phase cells of *S. mutans* NCTC 10832 to solutions containing sucrose, xylitol or 4,1',6'-trichloro-4,1',6'-trideoxygalactosucrose (compound no. 5 also referred to herein as "TGS") or combinations of sucrose with xylitol or TGS, each solution being 0.05 molar with respect to each saccharide. Plain aqueous solutions were used and also solutions containing amino acids (protein hydrolysate) 1% w/v to approximate the buffering effect of natural saliva. Control experiments were effected using no saccharide in order to illustrate the endogenous metabolism of the organism. Each experiment was quadruplicated and was run at 37° C. The pH was measured at 0, 0.5, 1, 1.5, 2, 3 and 4 hours. The results were as shown in the following table:

| Saccharide | Amino acids | \multicolumn{7}{c}{Time (h)} | | | | | | |
|---|---|---|---|---|---|---|---|---|
| | | 0 | 0.5 | 1.0 | 1.5 | 2.0 | 3.0 | 4.0 |
| Sucrose | − | 5.69 | 4.57 | 4.57 | 4.58 | 4.54 | 4.63 | 4.55 |
| Sucrose | + | 5.98 | 5.55 | 5.36 | 5.10 | 5.00 | 4.92 | 4.79 |
| Xylitol | − | 5.94 | 5.50 | 5.42 | 5.39 | 5.32 | 5.38 | 5.37 |
| TGS | − | 5.88 | 5.67 | 5.69 | 5.69 | 5.61 | 5.67 | 5.63 |
| Sucrose/xylitol | − | 5.93 | 4.63 | 4.61 | 4.76 | 4.54 | 4.68 | 4.66 |
| Sucrose/xylitol | + | 6.03 | 5.64 | 5.38 | 5.21 | 5.08 | 4.92 | 4.82 |
| Sucrose/TGS | − | 6.27 | 5.05 | 4.90 | 4.86 | 4.75 | 4.94 | 4.80 |
| Sucrose/TGS | + | 5.98 | 5.67 | 5.47 | 5.35 | 5.26 | 5.13 | 5.03 |
| None | − | 5.83 | 5.37 | 5.27 | 5.25 | 5.27 | 5.31 | 5.29 |
| None | + | 6.00 | 5.93 | 5.88 | 5.87 | 5.86 | 5.83 | 5.76 |

The data were analysed by the Duncan Procedure which indicated that there were no statistically significant differences among treatments grouped together in the sub-sets shown in the following Table:

| Sub-set | Solution | Mean pH |
|---|---|---|
| a | Sucrose | 4.57 |
|   | Sucrose/xylitol | 4.63 |
| b | Sucrose/TGS | 4.82 |
|   | Sucrose/amino acids | 4.91 |
| c | Sucrose/amino acids | 4.91 |
|   | Sucrose/amino acids/xylitol | 4.94 |
| d | Sucrose/amino acids/TGS | 5.14 |
| e | None | 5.30 |
|   | Xylitol | 5.36 |
| f | TGS | 5.64 |

| Sub-set | Solution | Mean pH |
|---|---|---|
| g | None/amino acids | 5.82 |

From these results, it will be seen that the inclusion of xylitol never had a statistically significally effect (consider, in turn, the carbohydrates grouped as sub-set a, sub-set c, and sub-set e). Thus xylitol is non-cariogenic but not anti-cariogenic.

On the other hand, the TGS always had a favourable effect which was statistically significant. Thus, the addition of TGS to sucrose reduced the amount of acid produced, as did the addition of TGS to the mixture of sucrose and amino acids. Moreover, the TGS on its own had a favourable effect against the endogenous metabolism of the micro-organism, whereas xylitol gave about the same mean pH as when carbohydrate was excluded.

(B) Adherence to teeth:

The extent to which cells of *S. mutans* adhere to teeth was investigated using a recognized model system. Solutions of the same substances as in (A) were made up, and the degree of deposition of suspended cells on to glass was studied using a "Magiscan" image analyser (Talyer et al., 1978 Praktischen Metallographie, Sonderbande 8: 433–442).

The results were as shown in the following Table:

| Carbohydrate | Amino acid | Coverage (%) | |
|---|---|---|---|
| | | After 0.5 h | After 4.0 h |
| Sucrose | − | 37.28 | 65.83 |
| Sucrose | + | 31.89 | 75.95 |
| Xylitol | − | 42.31 | 74.21 |
| TGS | − | 30.42 | 64.81 |
| Sucrose/xylitol | − | 35.32 | 62.30 |
| Sucrose/xylitol | + | 33.55 | 83.62 |
| Sucrose/TGS | − | 27.47 | 64.92 |
| Sucrose/TGS | + | 26.49 | 64.43 |
| None | − | | |
| None | + | | |

Note:
Each reading is the mean of 40 determinations.

As analysed by the Mann Whitney U-test, the results show the TGS reduces the degree of adhesion significantly and that the reduction is greater than that of xylitol. Indeed, in the presence of amino acids xylitol appeared to cause an increase rather than a decrease.

Additionally, scanning electron microscopy of glass with adherent cells revealed a qualitative difference in adhering material. Adherent cells deposited from a sucrose medium characteristically clumped and were coated with extracellular polysaccharide. Addition of TGS, on the other hand, was found to reduce the extracellular coating and the size of the clumps. No such effect was observed in the case of xylitol.

(C) Further tests on pH reduction:

Twelve sets of tests were carried out in the same way as described above at (A) but using solutions which were 0.055 molar in the respective chlorodeoxy derivative.

Solutions of the following were employed:
(i) Saline, negative control for endogenous metabolism
(ii) Sucrose, positive control
(iii) 6,1',6'-trichloro-6,1',6'-trideoxysucrose, compound no. 7.
(iv) Compound no. 7 plus sucrose.

(v) 1',6'-dichloro-1',6'-dideoxysucrose, compound no. 4

(vi) Compound no. 4 plus sucrose (vii) 4,1',6'-trichloro-4,1',6'-trideoxygalactosucrose, Compound no. 5.

(viii) Compound no. 5 plus sucrose (ix) 4,6,6'-trichloro-4,6,6'-trideoxygalactosucrose, Compound no. 6

(x) Compound no. 6 plus sucrose (xi) 1'-chloro-1'-deoxysucrose, compound no. 1

(xii) Compound no. 1 plus sucrose

The acid production was monitored as before. There was a tendency for the pH to level off after 2 hours, and accordingly the data for 2, 3 and 4 hours was pooled and subjected to statistical analysis. By analysis in accordance with the Duncan procedure, the sub-sets were identified as shown in the following table:

| Sub-set | Solution | Mean pH |
|---------|----------|---------|
| a | (ii) | 4.33 |
| b | (vi) | 4.59 |
| c | (xii) | 4.81 |
|   | (x) | 4.82 |
| d | (xi) | 5.09 |
|   | (ix) | 5.20 |
| e | (ix) | 5.20 |
|   | (viii) | 5.30 |
|   | (iv) | 5.33 |
| f | (viii) | 5.30 |
|   | (iv) | 5.33 |
|   | (i) | 5.43 |
| g | (iv) | 5.33 |
|   | (i) | 5.43 |
|   | (v) | 5.48 |
| h | (iii) | 6.48 |
| i | (vii) | 6.82 |

Sub-set a is the sucrose solution, and all of the other solutions gave a statistically significant decrease in the amount of acid produced. The compounds no. 7 and no. 5 are especially effective, since the solutions (iv) and (vii) both resulted in a pH which was one pH unit less than that of solution (ii), sucrose with no added chlorodeoxysucrose. Particularly striking are the sub-sets h and i, where solutions of the respective compounds 1 and 5 give a better result than the negative control, saline, which is grouped in sub-set g.

(D) Further tests on adherence to teeth:

While recording the pH during the tests of (C), the adherence was monitored in the same way as in (B). The percentage coverage of a glass slide was determined at 0.5 and 4 hours for each solution, and the results treated by the Duncan procedure. The sub-sets were as follows:

| Sub-set | After 0.5 hours Solution | % coverage |
|---------|--------------------------|------------|
| a | (xii) | 27.5 |
|   | (iv) | 28.5 |
| b | (iv) | 28.5 |
|   | (iii) | 29.7 |
| c | (xi) | 35.6 |
| d | (viii) | 38.2 |
| e | (vii) | 41.4 |
|   | (x) | 42.7 |
| f | (i) | 49.4 |
| g | (ii) | 51.2 |
|   | (v) | 51.6 |
|   | (ix) | 51.6 |
|   | (vi) | 51.8 |

Four of the five tested compounds reduced adherence of the cells in the presence of sucrose, with only compound no. 4 falling in the sub-set g which includes sucrose itself. The most active compounds at 0.5 hours are compounds no. 1 and no. 7.

| Sub-set | After 4 hours Solution | % coverage |
|---------|------------------------|------------|
| a | (iv) | 30. |
| b | (xii) | 38.4 |
| c | (viii) | 45.9 |
| d | (xi) | 52.3 |
|   | (iii) | 54.2 |
| e | (vii) | 58.4 |
| f | (x) | 64.3 |
| g | (vi) | 68.2 |
|   | (ii) | 69.2 |
|   | (v) | 70.3 |
|   | (ix) | 70.8 |
| h | (i) | 75.3 |

Equally as with the test after 0.5 hours, these results show that only compound no. 4 did not reduce the adherence. Compounds no. 1 and no. 7 were again the most active.

(E) Tests using rats:

Studies were carried out on the effect of chlorodeoxysucroses on cariogenic food products, using 4,1',6'-trichloro-4,1',6'-trideoxygalactosucrose as the chlorodeoxysucrose. Cariogenicity was examined using the gnotobiotic rat caries model (see for example Drucker and Green, Arch. Oral Biol. Vol 23 pp 183–187).

The experiment involved the use of germ-free Liverpool hooded rats inoculated orally with *Streptococcus mutans* NCT 10823 (a caries-producing organism). The rats were fed a diet consisting essentially of 33% by weight skim milk and 67% by weight carbohydrate. The carbohydrate consisted of (i) starch, or (ii) sucrose, or (iii) starch together with sufficient of the chlorodeoxysucrose to give a sweetness as perceived by a human of the same order as that of the sucrose. After 21 days, the rats were sacrificed and the lower jaw lesions were counted to give a caries score for each rat (see Konig, Marthaler and Muhlemann, Dt. Zahn-Mund-u. Kieferheilk Vol. 29, 99–127).

A statistical analysis of the caries scores for each rat showed that, as expected, the starch diet was significantly less cariogenic than the sucrose diet and also that the chlorosucrose plus starch diet was less cariogenic than the sucrose diet. This would be expected, since the proportion of the chlorodeoxysucrose was extremely small, less than 0.2 g.

However, the results also showed that, surprisingly, the starch plus chlorosucrose diet was less cariogenic than the starch diet, thus indicating that the chlorodeoxysucrose appeared to be decreasing the cariogenicity of the starch.

(F) Tests using human volunteers:

The compound 4,1',6'-trichloro-4,1',6'-trideoxygalactosucrose was selected as a suitable candidate for further testing. A mouthrinse in accordance with the invention was prepared using the selected compound as active ingredient. The level of the active ingredient was initially chosen to be such that the mouthrinse tasted the same as a 15% w/v solution of sucrose.

Six subjects were used, who were first acquainted with the available toxicological data and who subsequently agreed to take part in the tests. The subjects were instructed not to clean their teeth on their day of testing. At sampling time, 0 min, each subject took 5% w/v glucose mouthrinse for 2 minutes, then waited a further 8 minutes before the buccal and lingual plaque of one side of the jaw (upper and lower) was removed and placed on aluminium foil and sealed. 8 ml of the mouthrinse in accordance with the invention was used for precisely 2 minutes, and the dental plaque from the other side of the jaw removed after a further 8 minutes, and placed on aluminum foil and sealed.

In order that differing concentrations of plaque did not give rise to different rates of acid production, samples of wet plaque were accurately weighed and suspended in sterile saliva at 10 mg wet weight $ml^{-1}$. Plaque was homogenised before testing.

Samples (0.2 ml) were tested after admixture with 0.1 ml 5% w/v glucose and 0.2 ml sterile saliva. The pH was monitored in quadruplicated tests.

The pH fell throughout each test.

Graphs of pH fall for individual subjects indicated a beneficial, antiacidogenic, effect of the mouthwash with active ingredient, except for two subjects. In these two cases the plaque control was rather less acidogenic than in the other cases and therefore any apparent failure was not a practical disadvantage. Conversely, the other four, more acidogenic plaques were all rendered less acidogenic by the active mouthwash.

All subjects believed that the mouthwash with active ingredient increased the yield of plaque, presumably by lessening adherence.

Pooling of data at different times was not justifiable, and the Duncan procedure could not be followed. Data was therefore analysed by computer using an 'Analysis of Variance' program and a 'Description of Populations' program.

As part of the treatment of the data pooled for the six subjects, the significance of the beneficial effect on acidogenicity of plaque was determined. The probability, 'p', was as shown in the following Table:

| Time (h) | 'p' |
|---|---|
| 0.5 | 0.008 |
| 1.0 | 0.003 |
| 2.0 | 0.046 |
| 3.0 | 0.509 |
| 4.0 | 0.172 |
| 22.0 | 0.600 |

The probability values at 0.5, 1.0 and 2.0 hours are exceptionally low, indicating a real decrease in pH drop i.e. a true antiacidogenic effect.

The tests were supplemented by re-testing one subject without a glucose-pre-rinse. Samples taken were an untreated plaque control, and a post-mouthrinse plaque.

Again there was a beneficial effect by using the mouthrinse of the invention. The significance was as shown in the following table:

| Time (h) | 'p' |
|---|---|
| 0.5 | 0.001 |
| 1.0 | 0.001 |
| 1.5 | 0.001 |
| 2.0 | 0.004 |
| 2.5 | 0.131 |
| 3.0 | 0.023 |
| 3.5 | 0.509 |
| 4.0 | 0.603 |

An antiacidogenic effect is strongly indicated by these results.

The compound 6,1',6'-trichloro-6,1',6'-trideoxysucrose was also selected as a suitable candidate for further testing in the same way on human volunteers. A mouthrinse was prepared using the compound at a level such that the mouthrinse had the same sweetness as a 15% w/v solution of sucrose. Statistically conclusive proof that the mouthrinse was evincing an anti-acidogenic effect was not available, though all subjects again perceived that the mouthwash increased the yield of plaque, presumably by lessening adherence.

Given that the chlorodeoxysucrose derivatives (I) exhibit an anti-cariogenic effect, the skilled man will have no difficulty in formulating dental compositions which employ them as an active ingredient. Suitable compositions include toothpastes and tooth powders; mouthrinse; pastilles, lozenges and other forms for retention in the mouth until dissolved; and chewing gums.

The following formulations are given by way of non-limiting example.

EXAMPLE 1

| Mouthwash | |
|---|---|
| Ingredient | Percent by Weight |
| Humectant, glycerine | 10 |
| Solvent, ethyl alcohol | 10 |
| Flavour | 1 |
| Surfactant | 0.1 |
| TGS | 0.02 |
| Water | to 100 |

This mouthwash has a sweet taste which can be modified if desired by addition of known additives e.g. to give a more astringent flavour.

EXAMPLE 2

| Tooth paste | |
|---|---|
| Ingredient | Percent by Weight |
| Abrasive, calcium pyrophosphate | 45 |
| Humectant, glycerine | 25 |
| Surfactant | 3 |
| Binder | 1 |
| Soluble Fluoride | 0.09 |
| TGS | 0.009 |
| Peppermint flavour | 1.1 |
| Water | to 100 |

EXAMPLE 3

| Chewing Gum | |
|---|---|
| Ingredient | Parts by Weight |
| Gum rubber base | 25 |
| Glucose syrup | 15 |
| Spearmint oil | 1.2 |
| Calcium carbonate | 1.8 |
| TGS | 0.005 |

I claim:

1. A method of preventing or limiting dental caries by administering to the subject an anticariogenic-effective amount of a chlorodeoxysucrose derivative of the general formula

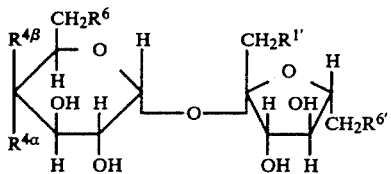

(II)

wherein:

R$^{4\alpha}$ is a hydroxy group and R$^{4\beta}$ is a hydrogen atom, or, one of R$^{4\alpha}$ and R$^{4\beta}$ is a hydrogen atom and the other is a chlorine atom;

R$^6$ is a hydroxy group or, if at least one of R$^{4\alpha}$, R$^{4\beta}$ or R$^{1'}$ is a chlorine atom, then it is a hydroxy group or a chlorine atom;

R$^{1'}$ is a hydroxy group or a chlorine atom; and

R$^{6'}$ is a hydroxy group, or if at least one of R$^{4\alpha}$, R$^{4\beta}$ or R$^{1'}$ is a chlorine atom, then it is a hydroxy group or a chlorine atom.

2. A method of reducing acidogenesis by mouth flora in the presence of a carbohydrate, comprising contacting the flora in the mouth with a chlorodeoxysucrose derivative of the general formula (II) as defined in claim 1.

3. A method of reducing the adhesion of cells of mouth flora to dental surfaces and of reducing plaque formation thereon, comprising contacting the teeth with a chlorodeoxysucrose derivative of the general formula (II) as defined in claim 1.

4. The method of claim 1, 2 or 3, wherein the chlorodeoxysucrose derivative is 4,1',6'-trichloro-4,1',6'-trideoxygalactosucrose.

5. The method of claim 1, 2 or 3, wherein the chlorodeoxysucrose derivative is 1'-chloro-1'-deoxysucrose or 6,1',6'-trichloro-6,1',6'-trideoxysucrose.

6. The method of claim 1, 2 or 3, wherein the amount of the chlorodeoxysucrose derivative is less than $15.(x)^{-1}$ weight percent where x is the sweetening power relative to a 10% sucrose solution.

7. The method of claim 1, 2 or 3, wherein the chlorosucrose derivative is 1',6'-dichloro-1',6'-dideoxysucrose or 4-chloro-4-deoxy-α-D-galactopyranosyl-1-chloro-1-deoxy-β-D-fructofuranoside.

8. The method of claim 1 wherein said derivative is administered in the form of a dental composition containing less than 0.1 wt.% of said derivative.

* * * * *